United States Patent
Azizian et al.

(10) Patent No.: US 12,310,670 B2
(45) Date of Patent: May 27, 2025

(54) SYSTEM AND METHOD RELATED TO REGISTRATION FOR A MEDICAL PROCEDURE

(71) Applicant: INTUITIVE SURGICAL OPERATIONS, INC., Sunnyvale, CA (US)

(72) Inventors: Mahdi Azizian, Santa Clara, CA (US); Maximilian Hunter Allan, San Francisco, CA (US); Wen Pei Liu, San Jose, CA (US); Angus Jonathan McLeod, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 362 days.

(21) Appl. No.: 17/620,081

(22) PCT Filed: Jun. 24, 2020

(86) PCT No.: PCT/US2020/039391
§ 371 (c)(1),
(2) Date: Dec. 16, 2021

(87) PCT Pub. No.: WO2020/264003
PCT Pub. Date: Dec. 30, 2020

(65) Prior Publication Data
US 2022/0323157 A1    Oct. 13, 2022

Related U.S. Application Data

(60) Provisional application No. 62/866,209, filed on Jun. 25, 2019.

(51) Int. Cl.
*A61B 34/20* (2016.01)
*A61B 34/10* (2016.01)

(52) U.S. Cl.
CPC .............. *A61B 34/20* (2016.02); *A61B 34/10* (2016.02); *A61B 2034/2046* (2016.02)

(58) Field of Classification Search
None
See application file for complete search history.

(56) References Cited

U.S. PATENT DOCUMENTS 9,095,252 B2    8/2015   Popovic
2006/0078195 A1  4/2006   Vaillant et al.
(Continued)

FOREIGN PATENT DOCUMENTS

CN    102917647 A    2/2013
CN    102999902 A    3/2013
(Continued)

OTHER PUBLICATIONS

Bhattacharya et al., "Multimodality medical image registration and fusion techniques using mutual information and genetic algorithm-based approaches". Adv. Exp. Med. Biol. 2011, vol. 696, Software Tools and Algorithms for Biological Systems. Chapter 44, pp. 441-449. (Year: 2011).*

(Continued)

*Primary Examiner* — Yi-Shan Yang
(74) *Attorney, Agent, or Firm* — Artegis Law Group, LLP

(57) ABSTRACT

A medical system includes one or more processors. The processors are configured to perform operations including receiving image data associated with an anatomic feature from a first imaging device. The image data is associated with a first imaging device space. Probe data associated with the anatomic feature is obtained from a second imaging device. The probe data is associated with a second imaging device space. The probe data is registered to the image data to generate a first registration between the second imaging device space and the first imaging device space. Anatomic (Continued)

model associated with the anatomic feature is registered to the probe data to generate a second registration between a model space of the anatomic model and the second imaging device space. A third registration between the model space and the first imaging device space is generated based on the first registration and the second registration.

15 Claims, 12 Drawing Sheets

(56) References Cited

U.S. PATENT DOCUMENTS

| | | | | |
|---|---|---|---|---|
| 2015/0369915 | A1* | 12/2015 | Eibye | G06F 9/5027 367/7 |
| 2018/0008355 | A1* | 1/2018 | Mozes | A61C 1/0015 |
| 2019/0290247 | A1* | 9/2019 | Popovic | A61B 1/0005 |

FOREIGN PATENT DOCUMENTS

| | | |
|---|---|---|
| CN | 104000655 A | 8/2014 |
| CN | 109219384 A | 1/2019 |
| WO | WO-2014186715 A1 | 11/2014 |
| WO | WO-2017207565 A1 | 12/2017 |

OTHER PUBLICATIONS

International Search Report and Written Opinion for Application No. PCT/US2020/039391, mailed Oct. 16, 2020, 15 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

International Preliminary Report on Patentability for Application No. PCT/US2020/039391 mailed on Jan. 6, 2022, 9 pages.

Office Action for Chinese Application No. CN202080046380.9, mailed Dec. 7, 2023, 20 pages.

Caramella D., et al., "3D Image Processing: Techniques and Clinical Applications," Tianjin Science and Technology Press, Aug. 2008, 7 Pages.

Junjie H., et al., "Fundamentals of Robotics Technology," Huazhong University of Science and Technology Press, Aug. 2018, 7 Pages.

Office Action for Chinese Application No. CN202080046360.9, mailed Jul. 27, 2024, 27 pages.

* cited by examiner

SYSTEM AND METHOD RELATED TO REGISTRATION FOR A MEDICAL PROCEDURE

RELATED APPLICATION

This application a U.S. National Stage patent application of International Patent Application No. PCT/US2020/039391, filed Jun. 24, 2020, the benefit of which is claimed, and claims the benefit of U.S. Provisional Application No. 62/866,209, filed Jun. 25, 2019, each of which is incorporated by reference herein.

TECHNICAL FIELD

The present disclosure is directed to systems for performing a medical procedure and more particularly to systems and methods for registering anatomic model to real-time image data during a medical procedure.

BACKGROUND

Medical robotic systems such as teleoperational systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical teleoperational systems is strong and growing.

Examples of medical teleoperational systems include the da Vinci® Surgical System and the da Vinci® S™ Surgical System from Intuitive Surgical, Inc., of Sunnyvale, Calif. Each of these systems includes an operator's console, a patient-side cart, a high performance three-dimensional ("3-D") vision system, and Intuitive Surgical's proprietary EndoWrist® articulating instruments, which are modeled after the human wrist. When added to the motions of manipulators holding the surgical instruments, these articulating instruments allow at least six degrees of freedom of motion to their end effectors, which is comparable to or even greater than the natural motions of open surgery.

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions an operator may insert minimally invasive medical instruments (including surgical, diagnostic, therapeutic, or biopsy instruments) to reach a target tissue location. To assist with reaching the target tissue location, the location and movement of the medical instruments may be correlated with pre-operative or intra-operative images of the patient anatomy. With the image-guided instruments correlated to the images, the instruments may navigate natural or surgically created passageways in anatomic systems such as the lungs, the colon, the intestines, the kidneys, the heart, the circulatory system, or the like. However, registering the anatomic model generated from pre-operative or intra-operative images to real-time image data provided by an imaging device may be computational expensive and time consuming, and the registration quality (e.g., accuracy, completeness, validity, consistency) may not be satisfactory, which may cause uncertainty in the image-guided procedure.

Accordingly, it would be advantageous to provide improved registration for performing image-guided procedures.

SUMMARY

The embodiments of the invention are best summarized by the claims that follow the description.

In some embodiments, a medical system includes one or more processors. The processors are configured to perform operations comprising: receiving image data associated with an anatomic feature of a patient from a first imaging device, the image data associated with a first imaging device space; obtaining probe data associated with the anatomic feature from a second imaging device, the probe data associated with a second imaging device space; registering the probe data to the image data to generate a first registration between the second imaging device space and the first imaging device space; registering an anatomic model associated with the anatomic feature to the probe data to generate a second registration between a model space of the anatomic model and the second imaging device space; and generating a third registration between the model space and the first imaging device space based on the first registration and the second registration.

In some embodiments, a method includes receiving image data associated with an anatomic feature of a patient from a first imaging device, the image data associated with a first imaging device space; obtaining probe data associated with the anatomic feature from a second imaging device, the probe data associated with a second imaging device space; registering the probe data to the image data to generate a first registration between the second imaging device space and the first imaging device space; registering an anatomic model associated with the anatomic feature to the probe data to generate a second registration between a model space of the anatomic model and the second imaging device space; and generating a third registration between the model space and the first imaging device space based on the first registration and the second registration.

In some embodiments, a non-transitory machine-readable medium comprises a plurality of machine-readable instructions which when executed by one or more processors associated with a medical device are adapted to cause the one or more processors to perform any of the operations or methods described herein.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

DETAILED DESCRIPTION

Figure 1A:
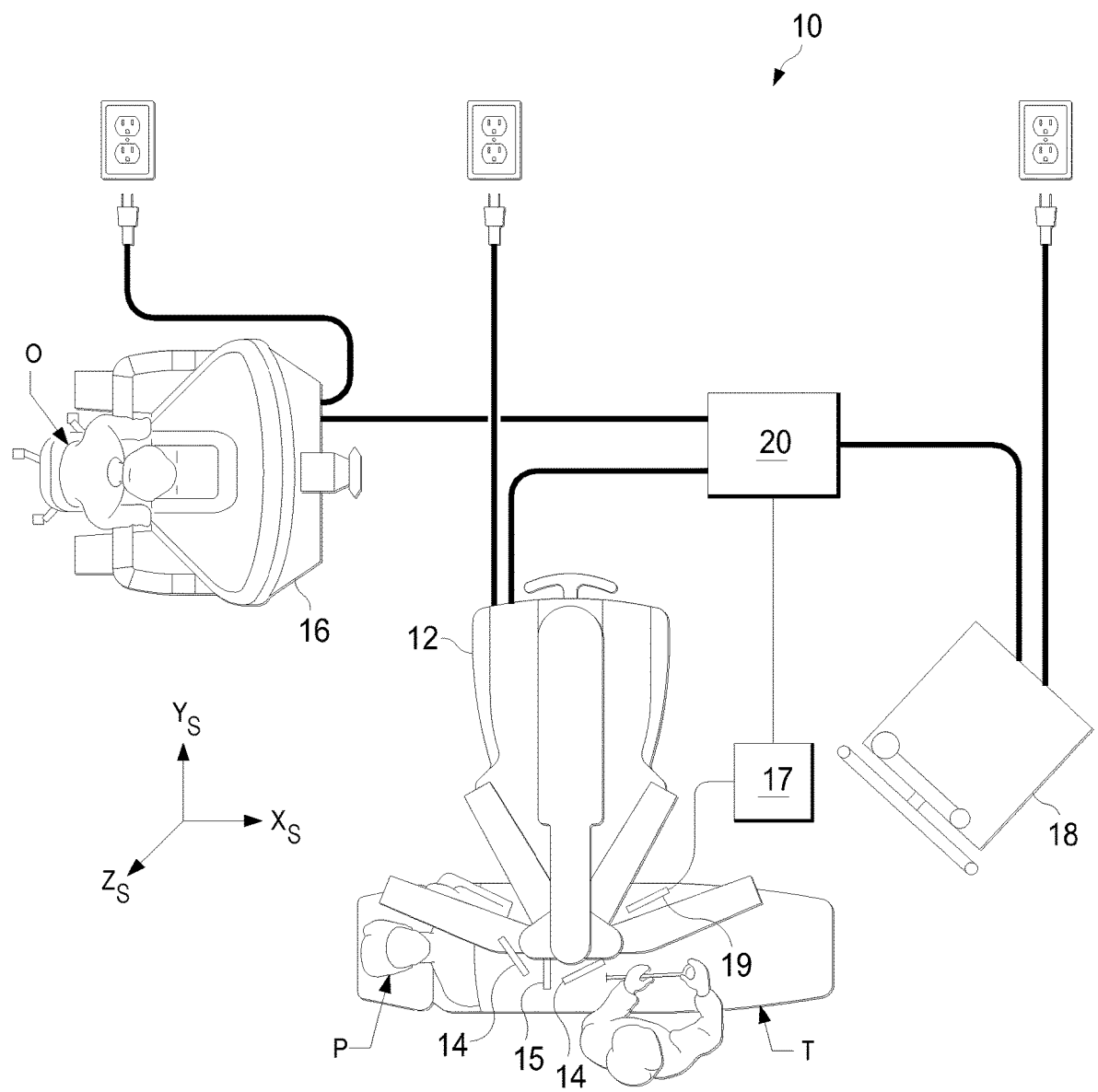
FIG. 1A is a schematic view of a teleoperated medical system in a surgical frame of reference, in accordance with an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances, well known methods, procedures, components, and circuits have not been described in detail so as to not unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Aspects of the invention are described primarily in terms of an implementation using a computer-aided medical system such as a da Vinci® Surgical System commercialized by Intuitive Surgical, Inc. of Sunnyvale, California. Knowledgeable persons will understand, however, that inventive aspects disclosed herein may be embodied and implemented in various ways, including robotic and, if applicable, non-robotic embodiments and implementations. Implementations on any surgical systems such as the da Vinci® Surgical Systems are merely exemplary and are not to be considered as limiting the scope of the inventive aspects disclosed herein. For example, any reference to surgical instruments and surgical methods is non-limiting as the tools, systems, and methods described herein may be used for animals, human cadavers, animal cadavers, portions of human or animal anatomy, tissue removed from human or animal anatomies (with or without return to a human or animal anatomy), non-surgical diagnosis, industrial systems, and general robotic or teleoperational systems. As further examples, the instruments, systems, and methods described herein may be used for non-medical purposes including industrial uses, general robotic uses, sensing or manipulating non-tissue work pieces, cosmetic improvements, imaging of human or animal anatomy, gathering data from human or animal anatomy, setting up or taking down systems, training medical or non-medical personnel, and/or the like. Additional example applications include use for procedures on tissue removed from human or animal anatomies (without return to a human or animal anatomy) and for procedures on human or animal cadavers. Further, these techniques can also be used for medical treatment or diagnosis procedures that include, or do not include, surgical aspects.

Referring to FIG. 1A of the drawings, a teleoperated medical system for use in, for example, medical procedures including diagnostic, therapeutic, or surgical procedures, is generally indicated by the reference numeral 10 and operates within a surgical environment having a surgical frame of reference coordinate system, XS, YS, ZS. As will be described, the teleoperated medical systems of this disclosure are under the teleoperated control of an operator. In alternative embodiments, a teleoperated medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1A, the teleoperated medical system 10 generally includes a teleoperated assembly 12 mounted to or near an operating table T on which a patient P is positioned. The teleoperated assembly 12 may be referred to as a patient side cart. A medical instrument system 14 and an endoscopic imaging system 15 are operably coupled to the teleoperated assembly 12. An operator console 16 allows an operator O (e.g., a surgeon or other type of clinician) to view images of or representing the surgical site and to control the operation of the medical instrument system 14 and/or the endoscopic imaging system 15. A supplemental imaging system 17 including a minimally invasive image capture probe 19 may be used with the medical instrument system 14 and endoscopic imaging system 15 as will be described below. Together with the patient side cart, the supplemental imaging system 17 may be known as a patient side system. The endoscopic imaging system 15 provides images of the external surfaces of anatomic structures within the surgical environment. The supplemental imaging system 17 may be an internal imaging system such as an ultrasound, x-ray, or gamma imaging system capable of imaging beyond the external surface of the anatomic structures.

The operator console 16 may be located at an operator's console, which is usually located in the same room as operating table T. It should be understood, however, that the operator O can be located in a different room or a completely different building from the patient P. The operator console 16 includes left and right eye displays for presenting the operator O with a coordinated stereo view of the surgical site that enables depth perception. The console 16 further includes one or more input control devices which cause the teleoperated assembly 12 to manipulate one or more instruments or the endoscopic imaging system. The input control devices can provide the same degrees of freedom as their associated instruments 14 to provide the operator O with telepresence, or the perception that the input control devices are integral with the instruments 14 so that the operator has a strong sense of directly controlling the instruments 14. To this end, position, force, and tactile feedback sensors (not shown) may be employed to transmit position, force, and tactile sensations from the instruments 14 back to the operator's hands through the input control devices. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperated assembly to provide the operator with telepresence, the perception that the control device(s) are integral with the instruments so that the operator has a strong sense of directly controlling instruments as if present at the surgical site. In other embodiments, the control device(s) may have more or fewer degrees of freedom than the associated medical instruments and still provide the operator with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The teleoperated assembly 12 supports and manipulates the medical instrument system 14 while the operator O views the surgical site through the console 16. An image of the surgical site can be obtained by the endoscopic imaging system 15, such as a stereoscopic endoscope, which can be manipulated by the teleoperated assembly 12 to orient the endoscope 15. An electronics cart 18 can be used to process the images of the surgical site for subsequent display to the operator O through the operator console 16. The number of medical instrument systems 14 used at one time will generally depend on the diagnostic or surgical procedure and the space constraints within the operating room among other factors. The teleoperated assembly 12 may include a kinematic structure of one or more non-servo-controlled links (e.g., one or more links that may be manually positioned and locked in place, generally referred to as a set-up structure) and a teleoperated manipulator. The teleoperated assembly 12 includes a plurality of motors that drive inputs on the medical instrument system 14. These motors move in response to commands from the control system (e.g., control system 20). The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperated medical system 10 also includes a control system 20. The control system 20 includes at least one memory and at least one processor (not shown), and typically a plurality of processors, for effecting control between the medical instrument system 14, the endoscopic system 15, the operator console 16, and monitors on the electronics cart 18. The control system 20 may also receive and process images from the supplemental imaging system 17. The electronics cart 18 may house components of the endoscopic imaging system 15, the supplemental imaging system 17, the control system 20 as well as monitors and processors for processing and displaying captured images.

The control system 20 also includes programmed instructions (e.g., a computer-readable medium storing the instructions) to implement some or all the methods described in accordance with aspects disclosed herein. While control system 20 is shown as a single block in the simplified schematic of FIG. 1A, the system may include two or more data processing circuits with one portion of the processing optionally being performed on or adjacent the teleoperated assembly 12, another portion of the processing being performed at the operator console 16, and the like. Any of a wide variety of centralized or distributed data processing architectures may be employed. Similarly, the programmed instructions may be implemented as a number of separate programs or subroutines, or they may be integrated into a number of other aspects of the teleoperated systems described herein. In one embodiment, control system 20 supports wireless communication protocols such as Bluetooth, IrDA, HomeRF, IEEE 802.11, DECT, and Wireless Telemetry.

In some embodiments, control system 20 may include one or more servo controllers that receive force and/or torque feedback from the medical instrument system 14. Responsive to the feedback, the servo controllers transmit signals to the operator console 16. The servo controller(s) may also transmit signals instructing teleoperated assembly 12 to move the medical instrument system(s) 14 and/or endoscopic imaging system 15 which extend into an internal surgical site within the patient body via openings in the body. Any suitable conventional or specialized servo controller may be used. A servo controller may be separate from, or integrated with, teleoperated assembly 12. In some embodiments, the servo controller and teleoperated assembly are provided as part of a teleoperated arm cart positioned adjacent to the patient's body.

The teleoperated medical system 10 may further include optional operation and support systems (not shown) such as illumination systems, steering control systems, irrigation systems, and/or suction systems. In alternative embodiments, the teleoperated system may include more than one teleoperated assembly and/or more than one operator console. The exact number of manipulator assemblies will depend on the surgical procedure and the space constraints within the operating room, among other factors. The operator consoles may be collocated, or they may be positioned in separate locations.

Figure 1B:
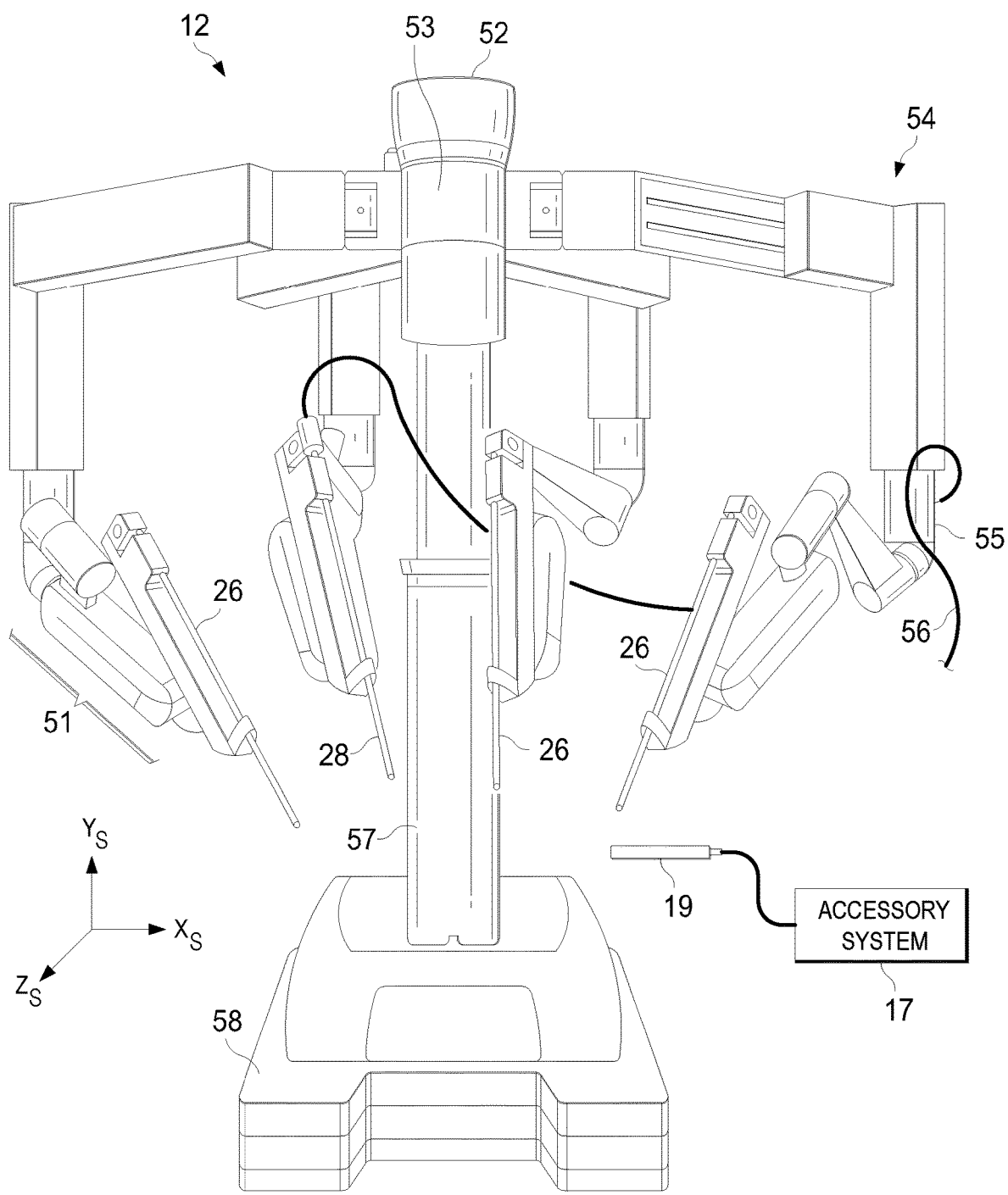
FIG. 1B is a perspective view of patient side systems, according to one example of principles described herein.

FIG. 1B is a perspective view of one embodiment of a teleoperated assembly 12 and an accessory system 17 which may, together, be referred to as a patient side system. The teleoperated assembly 12 shown provides for the manipulation of three surgical tools 26 (e.g., instrument systems 14) and an imaging device 28 (e.g., endoscopic imaging system 15), such as a stereoscopic endoscope used for the capture of images of the site of the procedure. The imaging device may transmit signals over a cable 56 to the electronics cart 18. Manipulation is provided by teleoperative mechanisms having a number of joints. The imaging device 28 and the surgical tools 26 can be positioned and manipulated through incisions or natural orifices in the patient so that a kinematic remote center is maintained at the incision to minimize the size of the incision. Images of the surgical site can include images of the distal ends of the surgical tools 26 when they are positioned within the field-of-view of the imaging device 28.

The teleoperated assembly 12 includes a drivable base 58. The drivable base 58 is connected to a telescoping column 57, which allows for adjustment of the height of the arms 54. The arms 54 may include a rotating joint 55 that both rotates and moves up and down. Each of the arms 54 may be connected to an orienting platform 53. The orienting platform 53 may be capable of 360 degrees of rotation. The teleoperated assembly 12 may also include a telescoping horizontal cantilever 52 for moving the orienting platform 53 in a horizontal direction.

In the present example, each of the arms 54 connects to a manipulator arm 51. The manipulator arms 51 may connect directly to surgical tools 26. The manipulator arms 51 may be teleoperable. In some examples, the arms 54 connecting to the orienting platform are not teleoperable. Rather, such arms 54 are positioned as desired before the operator begins operation with the teleoperative components.

Accessory system 17 may provide one or more functionalities that augment and/or complement the functionalities provided by surgical tools 26. Accessory system 17 includes an accessory 19 to provide the one or more additional functionalities. Accessory 19 may be a minimally invasive instrument sized for insertion into the surgical environment. Examples of accessories and their functionalities are discussed in greater detail below with reference to FIGS. 2A-7. Accessory 19 may include an endoscopic imaging system.

Endoscopic imaging systems (e.g., systems 15, 19, and/or 28) may be provided in a variety of configurations including rigid or flexible endoscopes. Rigid endoscopes include a rigid tube housing a relay lens system for transmitting an image from a distal end to a proximal end of the endoscope. Flexible endoscopes transmit images using one or more flexible optical fibers. Digital image-based endoscopes have a "chip on the tip" camera design in which a distal digital sensor such as a one or more charge-coupled device (CCD) or a complementary metal oxide semiconductor (CMOS) device acquire image data. Endoscopic imaging systems may provide two- or three-dimensional images of the endoscopic field of view (i.e. the imaging area) to the viewer. Two-dimensional images may provide limited depth perception. Three-dimensional stereo endoscopic images may provide the viewer with more accurate depth perception. Stereo endoscopic instruments employ stereo cameras to capture stereo images of the field of view of the patient anatomy. An endoscopic instrument may be a fully sterilizable assembly with the endoscope cable, handle and shaft all rigidly coupled and hermetically sealed.

Figure 2A:
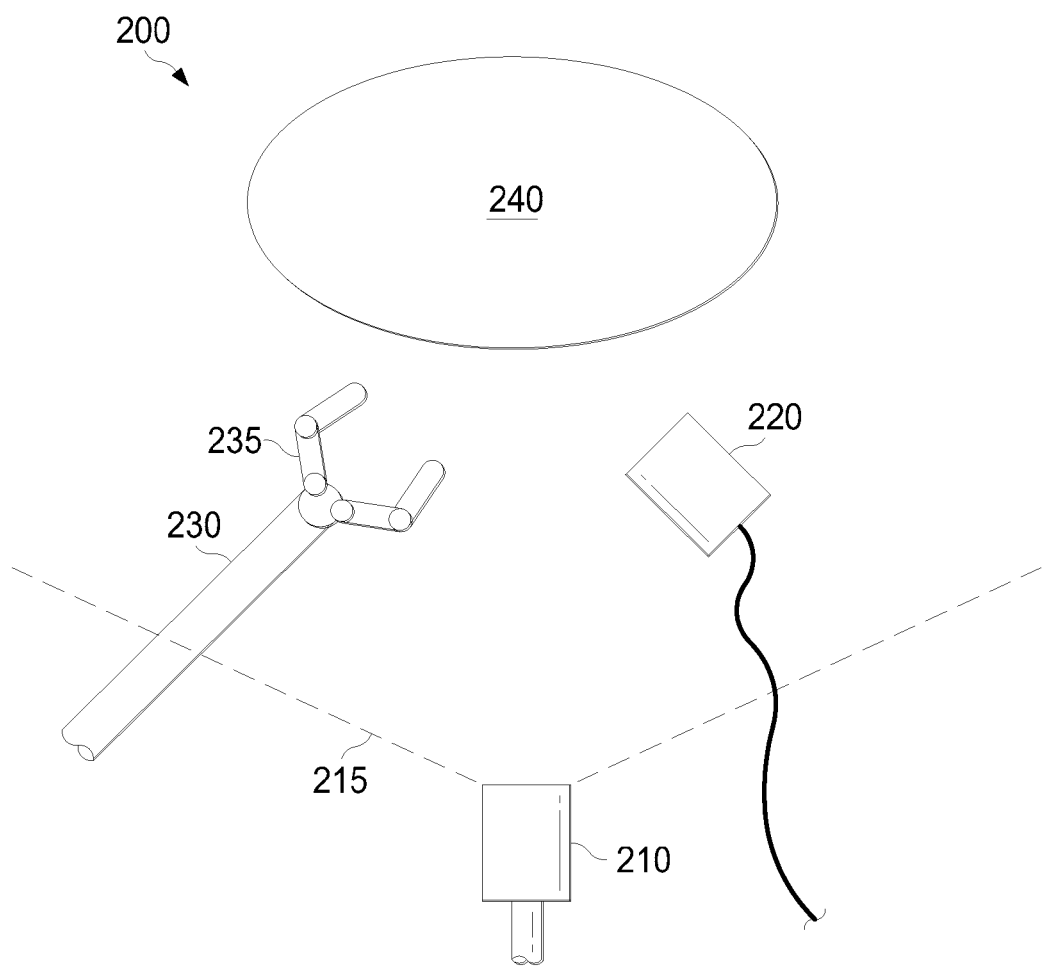
FIGS. 2A, 2B, and 2C are simplified diagrams of a system for registering an anatomic model to image data provided by an imaging device during a medical procedure according to some embodiments.
Figure 2B:
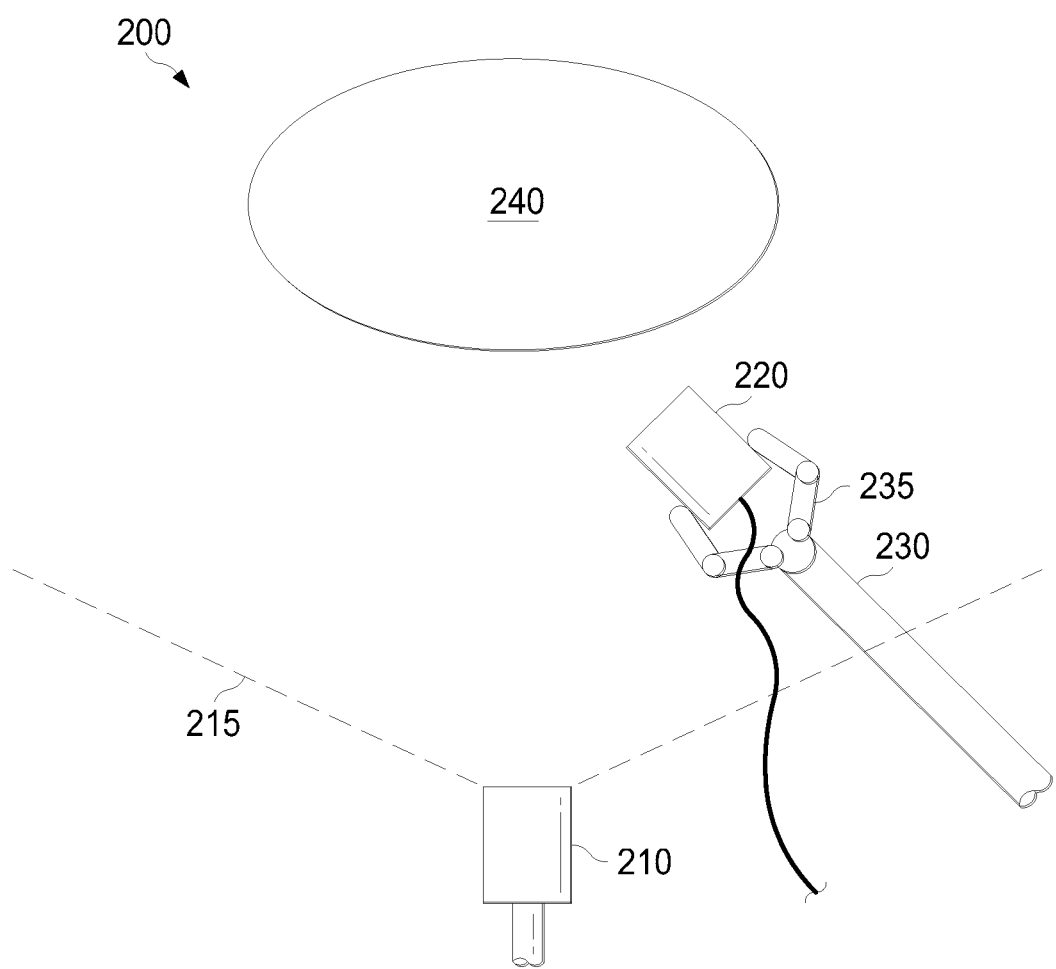
Figure 2C:
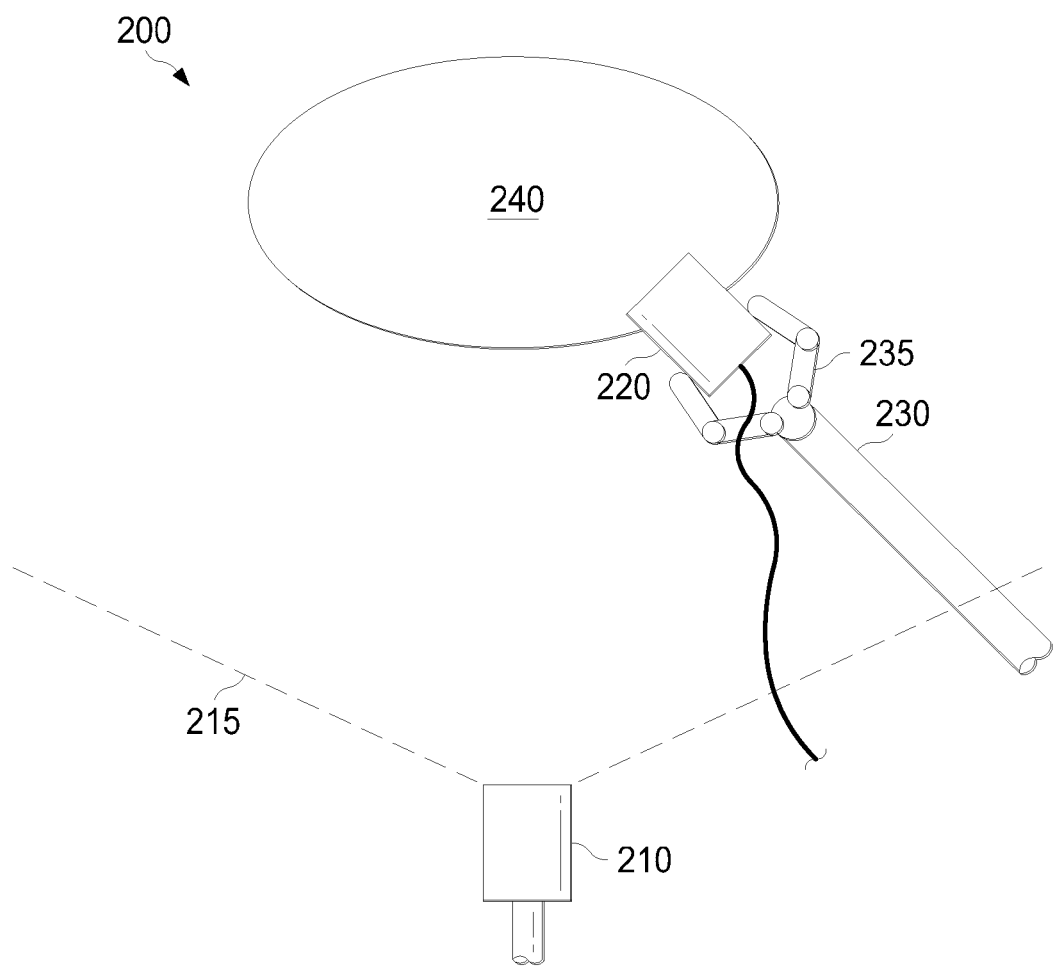
Figure 3A:
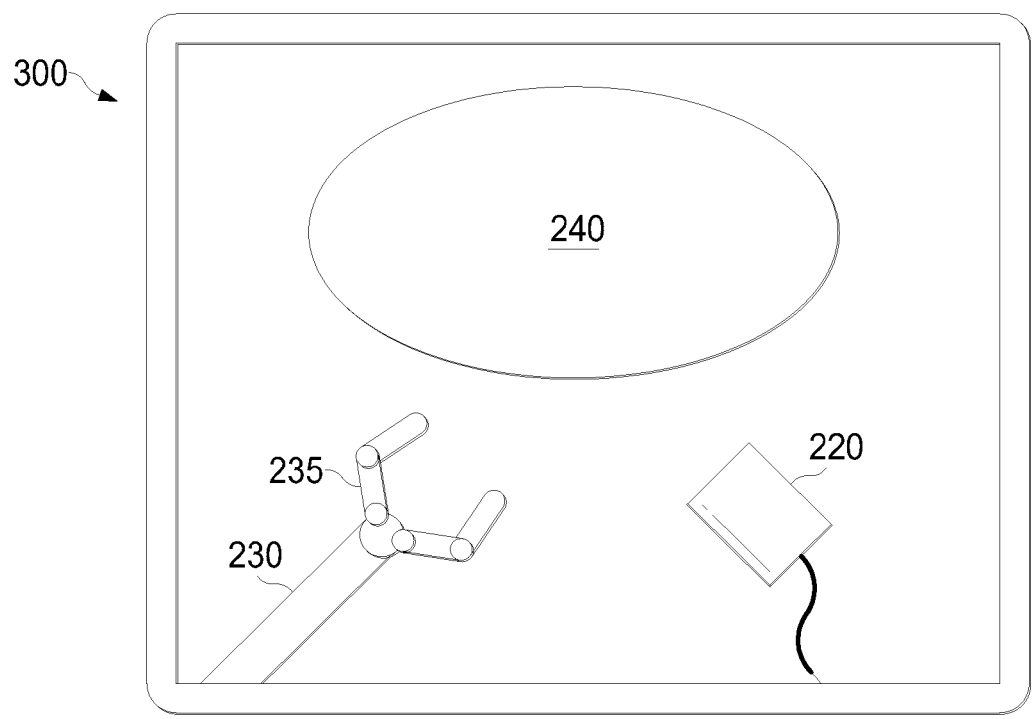
FIGS. 3A, 3B, and 3C are simplified diagrams of image data captured from imaging devices configured as depicted in FIGS. 2A-2C according to some embodiments.
Figure 3B:
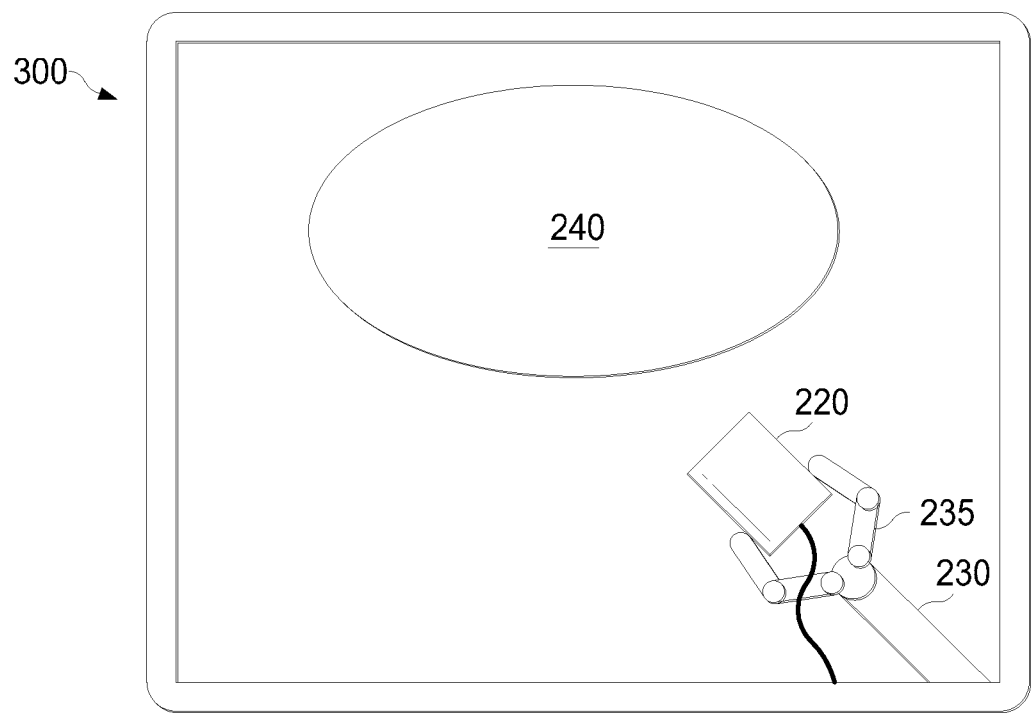
Figure 3C:
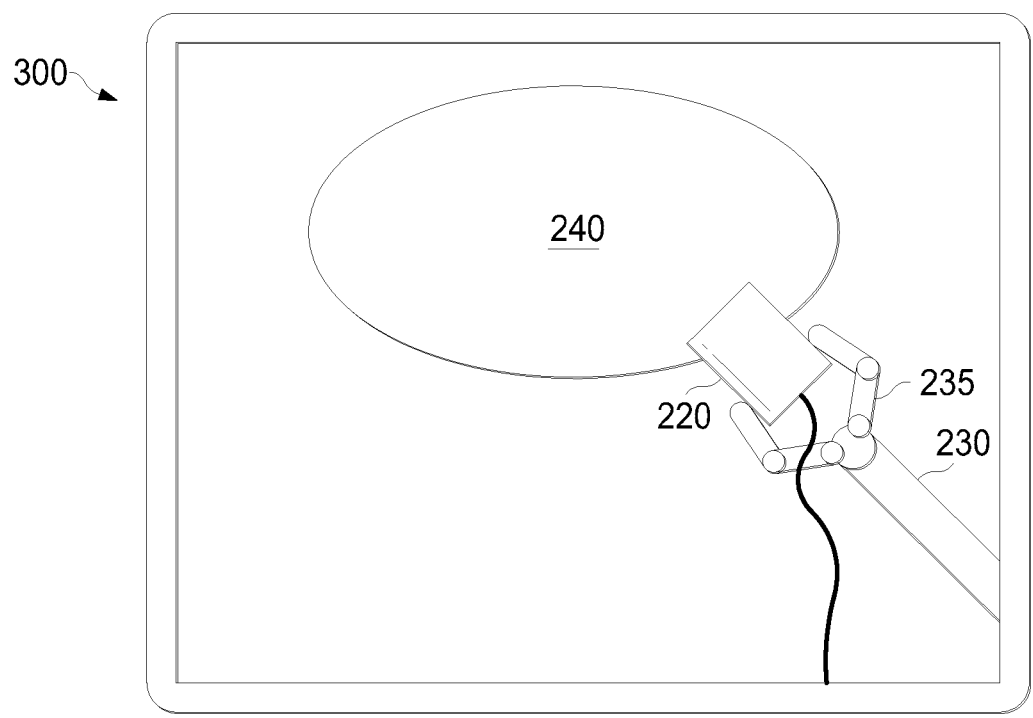

FIGS. 2A-2C are simplified diagrams illustrating a system 200 for registering an anatomic model to image data captured by an imaging device according to some embodiments. FIGS. 3A-3C are simplified diagrams illustrating image data 300 from imaging device 210 of system 200 as depicted in FIGS. 2A-2C respectively, according to some embodiments. In some embodiments, image data 300 may be displayed to an operator via a display of console 16 during a medical procedure.

Referring to the example of FIGS. 2A and 3A, a system 200 includes an imaging device 210 associated with an imaging area or a field of view 215. According to some embodiments, the imaging device 210 may generally correspond to an endoscope, such as an endoscope 15. The system 200 further includes a probe device 220. According to some embodiments, the probe device 220 may generally correspond to an accessory, such as accessory 19, a drop-in accessory, or the like. In some embodiments, probe device 220 includes an imaging device (e.g., an ultrasound probe) that uses a different imaging modality than imaging device 210, or the like.

System 200 may further include a medical instrument 230 with an end effector 235. According to some embodiments, medical instrument 230 may generally correspond to any of instruments 14. In some embodiments, end effector 235 may provide a mechanical, magnetic, or other type of gripping functionality (e.g., jaws) capable of gripping probe device 220.

As shown in the example of FIGS. 2A and 3A, an anatomic feature 240 is located within field of view 215 of imaging device 210. Anatomic feature 240 may include or correspond to a target of a medical procedure. For example, anatomic feature 240 may correspond to an organ (e.g., a kidney) that is being operated on during the medical procedure.

As shown in the example of FIGS. 2A and 3A, a probe device 220 is located within field of view 215 of imaging device 210. The probe device 220 may correspond to a drop-in device that is available for use during the medical procedure.

Referring to the example of FIGS. 2B and 3B, in some embodiments, an operator may control medical instrument 230 to grip and manipulate probe device 220.

Referring to the example of FIGS. 2C and 3C, the operator may scan anatomic feature 240, or a portion thereof, using probe device 220 by controlling medical instrument 230. The probe device 220 may generate probe data by scanning the anatomic feature 240.

Figure 4A:
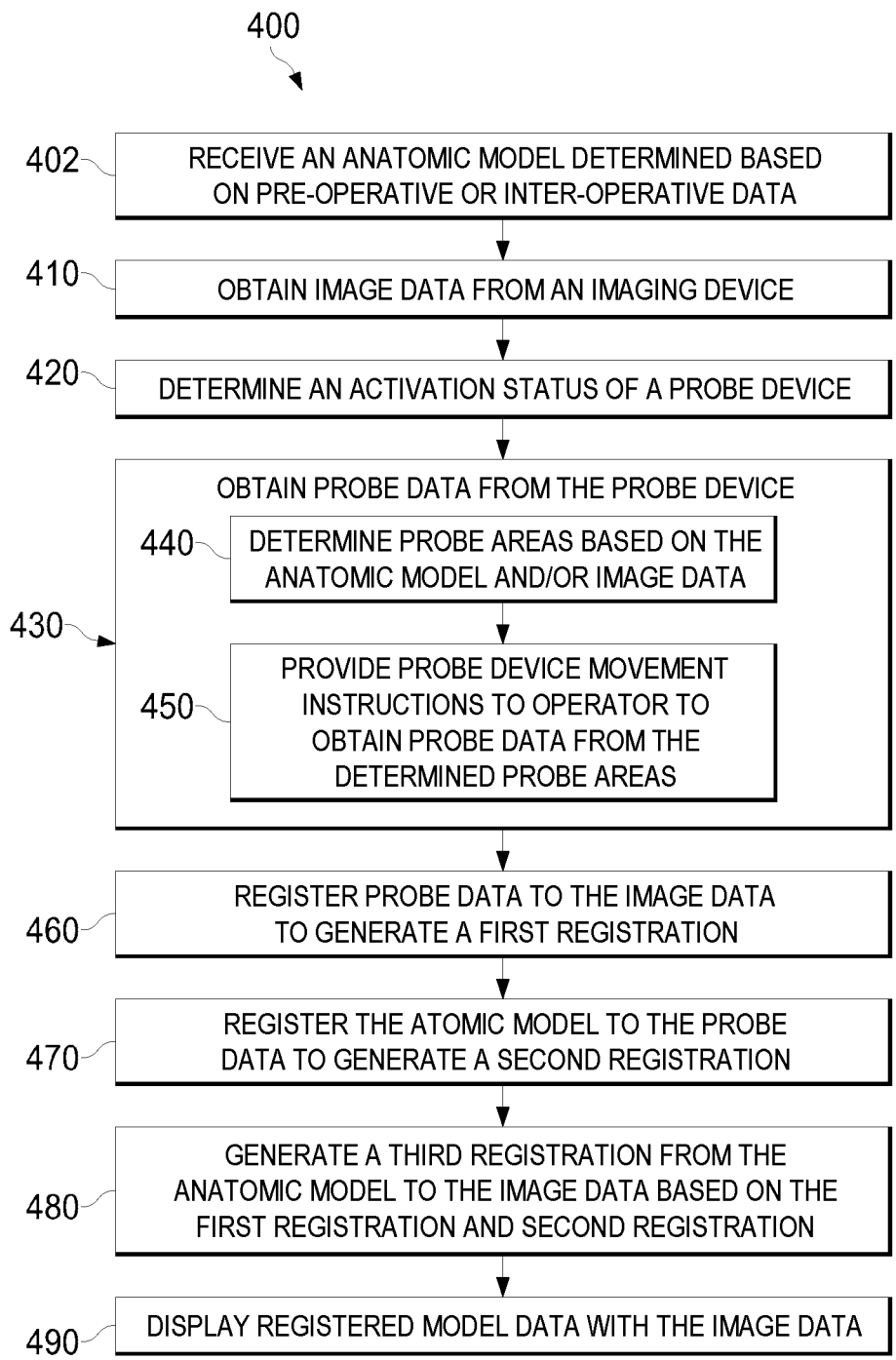
FIG. 4A is a flow chart illustrating a method for performing registration of an anatomic model to a patient anatomy in an image-guided surgical procedure or a portion thereof according to some embodiments.
Figure 4B:
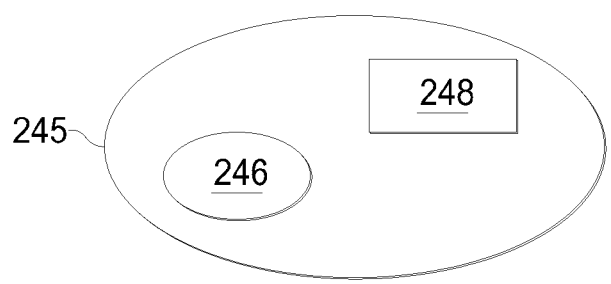
FIG. 4B illustrates an anatomic model with identified target probe areas according to some embodiments.
Figure 4C:
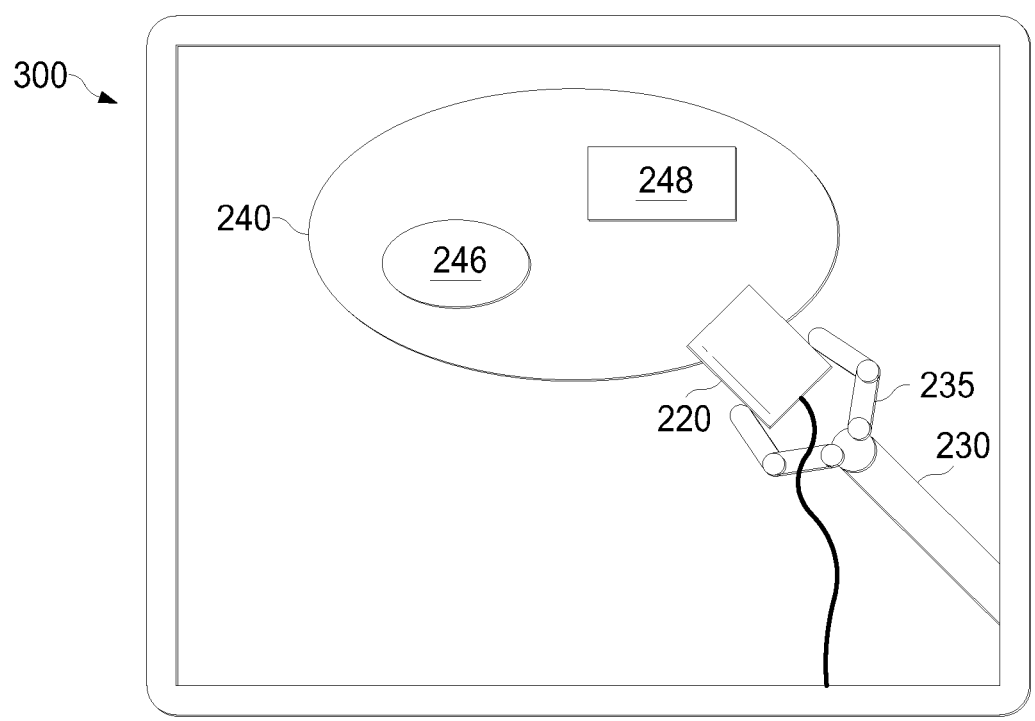
FIG. 4C illustrates estimated target probe areas corresponding to the identified target probe areas in image data according to some embodiments.
Figure 4D:
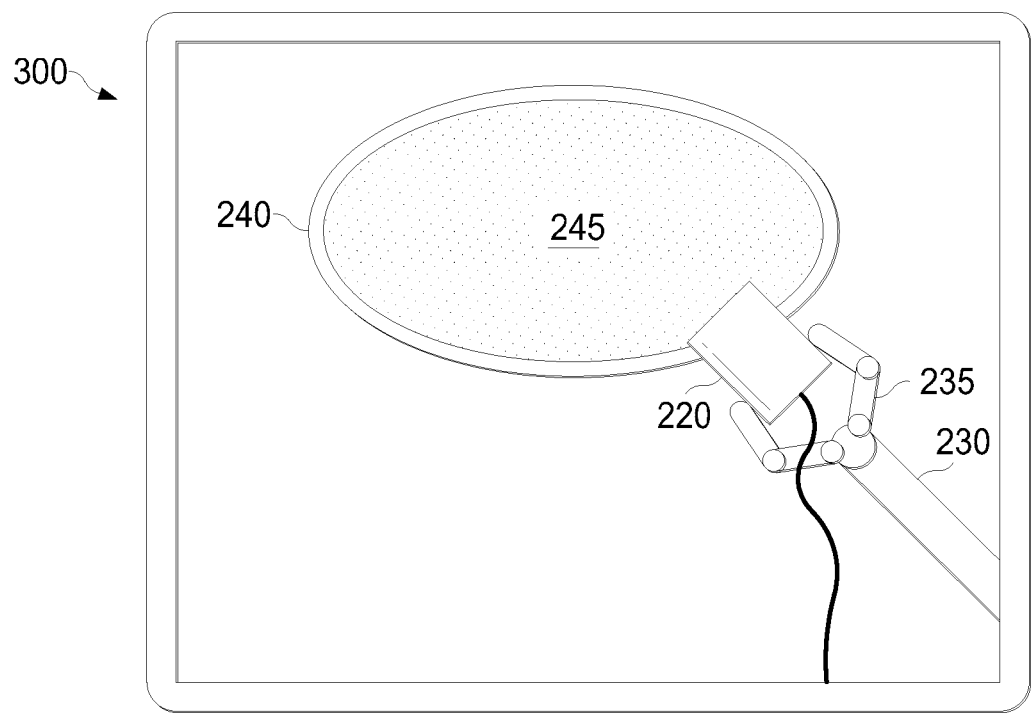
FIG. 4D is a display illustrating a registered anatomic model superimposed on image data according to some embodiments.
Figure 5:
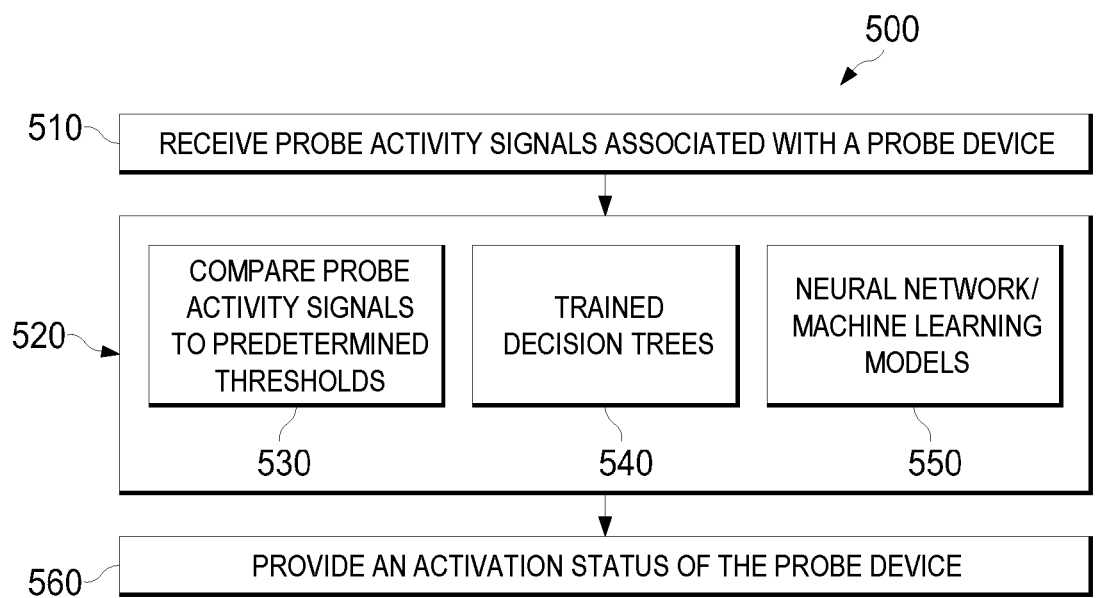
FIG. 5 is a flow chart illustrating a method for automatically determining an activation status of the probe device according to some embodiments.
Figure 6A:
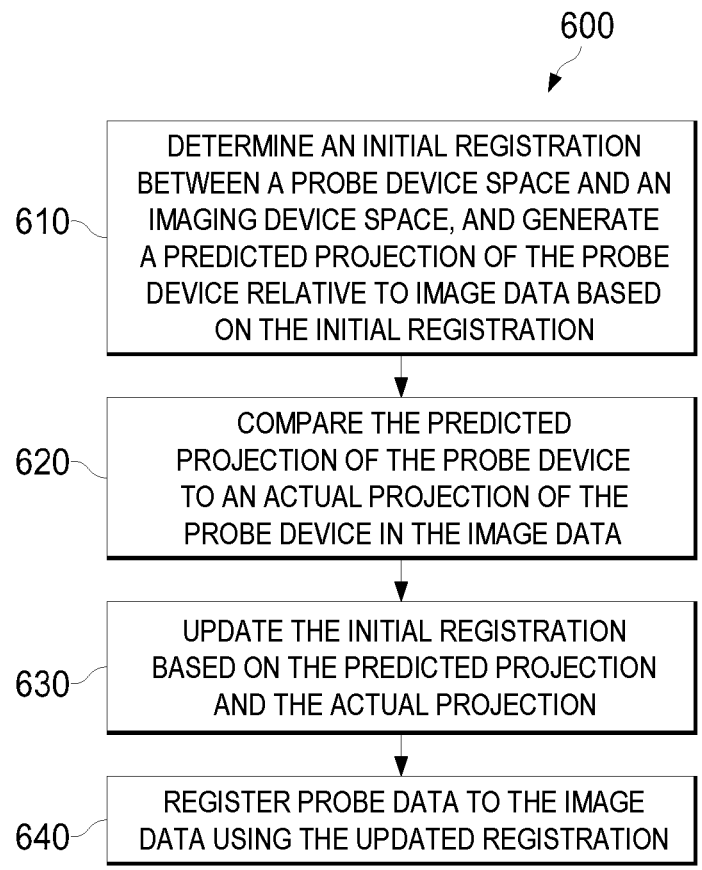
FIG. 6A is a flow chart illustrating a method for registering probe data to the image data in an image-guided surgical procedure according to some embodiments.
Figure 6B:
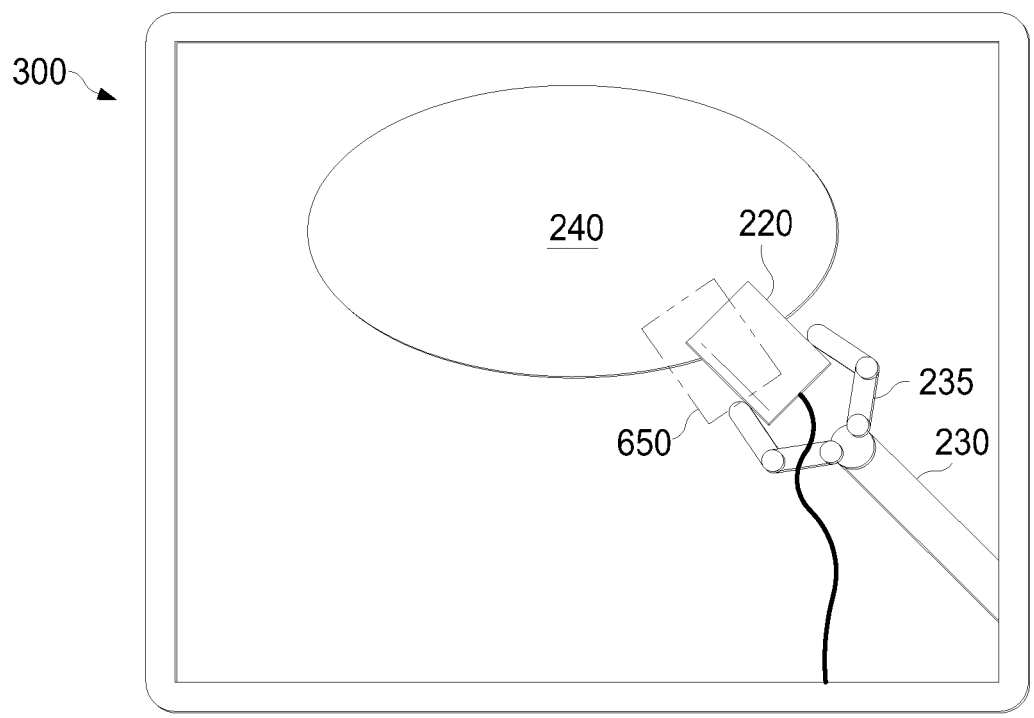
FIG. 6B is a display illustrating a projection of the probe device on image data during registering probe data to the image data according to some embodiments.
Figure 7:
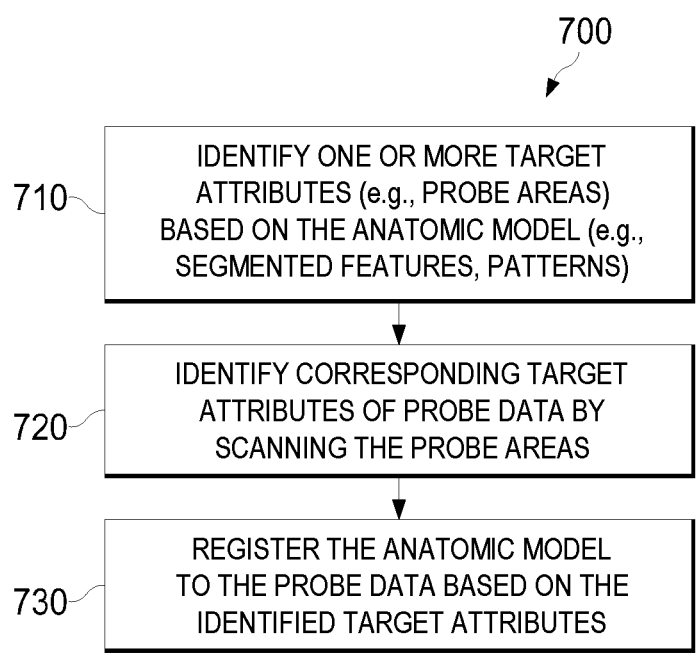
FIG. 7 is a flow chart illustrating a method for performing registration of an anatomic model to probe data in an image-guided surgical procedure according to some embodiments.

Referring to FIGS. 4A-7, in some embodiments, system 200 may use the probe data generated by a probe device 220 to register an anatomic model with image data 300 generated by an imaging device. FIG. 4A is a simplified diagram of a method 400 for registering an anatomic model to image data using probe data from the probe device 220 during a medical procedure. FIG. 4B illustrates an anatomic model with identified target probe areas. FIG. 4C is a display illustrating estimated target probe areas corresponding to the identified target probe areas in image data. FIG. 4D is a display illustrating a registered anatomic model superimposed on image data according to some embodiments. FIG. 4D illustrates a display where image data 300 is augmented to include an anatomic model superimposed on an anatomic feature 240 of image data 300 using the registration. FIG. 5 illustrates a method 500 for automatically detecting activation of a probe device for providing the probe data according to some embodiments. FIG. 6 illustrates a method 600 for registering probe data to image data according to some embodiments. FIG. 7 illustrates a method for registering an anatomic model to the probe data according to some embodiments.

FIG. 4A is a flowchart illustrating a method 400 for using the probe data generated by a probe device scanning anatomic feature 240 to register an anatomic model with image data 300 during a medical procedure. The method 400 is illustrated in FIG. 4A as a set of operations or processes 410 through 490. Not all of the illustrated processes 402 through 490 may be performed in all embodiments of method 400. Additionally, one or more processes that are not expressly illustrated in FIG. 4A may be included before, after, in between, or as part of the processes 402 through 490. In some embodiments, one or more of the processes may be implemented, at least in part, in the form of executable code stored on non-transitory, tangible, machine-readable media that when run by one or more processors (e.g., the processors of control system 20) may cause the one or more processors to perform one or more of the processes.

At process 402, an anatomic model 245 associated with the anatomic feature 240 is received. The anatomic model 245 is associated with a model space. In some embodiments, the anatomic model 245 is determined based on pre-operative data (e.g., using pre-operative CT scans) and/or inter-operative data model of the anatomic feature 240. In various embodiments, the anatomic model 245 may be a 2D or 3D model and may include various anatomic feature information of the anatomic feature 240. The anatomic feature information may include for example, a vasculature of the anatomic feature 240, particular blood vessel bifurcation(s) in the vasculature, speed and direction of blood flow of the vessels, etc.

At process 410, image data is obtained using an imaging device of system 200. The image data is associated with an imaging device space. In the example of FIGS. 2A-3C, imaging device 210 may be used to obtain image data 300 of a surgical site of a patient. The imaging device 210 records a concurrent or real-time image of a surgical site including the anatomic feature 240 and provides the image data to a processor (e.g., the processors of control system 20). The image data may be provided to an operator through one or more displays of medical system 10, such as one or more displays of console 16. The concurrent image may be, for example, a two- or three-dimensional image captured by an endoscope (e.g., endoscope 15) positioned within the surgical site.

At process 420, an activation status of a probe device is determined. In the examples of FIGS. 2A-3C, the activation status of the probe device 220 (e.g., an ultrasound probe) may be determined. In an example, the probe device 220 may be a drop-in accessory that lacks independent movement capabilities. The probe device 220 is referred to as being in an activated state when it is controllable by an operator and is referred to as being in an inactivated state when it is not controllable by the operator. In an example, an operator may control a medical instrument 230 with an end effector 235 to grip the probe device 220, and then control the probe device 220 by controlling the medical instrument 230. In that example, the probe device 220 is in an activated state. In another example, the probe device 220 is not controlled by any instruments controllable by the operator. In that example, the probe device 220 is in an inactivated state. In some embodiments, an operator may manually indicate the activation status (e.g., activated state or inactivated state) of the probe device 220 (e.g., using operator console 16). In some alternate embodiments, as discussed in detail with reference to FIG. 5 below, the activation status of the probe device 220 may be automatically determined. In some embodiments, at process 420, if it is determined that the probe device 220 has an activated state, the method 400 may proceed to processes 430 through 490 for receiving probe data from the probe device 220 and performing a registration from an anatomic model to imaging data based on the probe data. In some embodiments, at process 420, if it is determined that the probed device 220 has an inactivated state, the method 400 may wait until it is detected that the probe device 220 is in an activated state.

At process 430, the processors of control system 20 obtains the probe data from the probe device. In some embodiments, probe device 220 records a concurrent or real-time image of a surgical site including the anatomic feature 240 (e.g., by scanning the anatomic feature 240), and provides the probe data to a processor (e.g., the processors of control system 20). The probe data is associated with a probe device space. The probe data may be provided to an operator through one or more displays of medical system 10, such as one or more displays of console 16. In an example where the probe device 220 is an ultrasound device, the probe data includes ultrasound data. In various embodiments, the field of view of the probe device 220 may have a three-dimensional pyramidal frustum shape, a conical frustum shape, a slice-of-pie shape, or some other shape. In some embodiments, the probe device 220 provides a field of view that is different from the field of view of the imaging device 210.

In some embodiments, at process 430, the probe device 220 may scan the entire surface of the anatomic feature 240. Alternatively, in some embodiments, process 430 may use processes 440 and 450 to obtaining local probe data at particular local probe areas of the anatomic feature 240, which may reduce scanning time without affecting registration accuracy. Referring to FIG. 4B, at process 440, target probe areas 246 and 248 are determined based on anatomic feature elements (e.g., particular blood vessel bifurcation(s) in the vasculature, speed and direction of blood flow of the vessels, etc.) of the anatomic feature 240. Probe data from these probe areas 246 and 248 may be used for more accurate registration between the probe data and the anatomic model 245 (e.g., using feature-based registration in image processing algorithms to map those anatomic feature elements in the probe data and the anatomic model 245). In some embodiments, the processor may determine, based on the anatomic model 245 and its anatomic feature element information, whether a 2D model (e.g., a cross section) or a 3D model from probe data of a particular probe area is used for improved registration between the probe data and the anatomic model 245. In an example, the processor determines that probe area 246 includes a single blood vessel bifurcation, and a 2D model from probe data is suitable for the registration. In another example, the processor determines that probe area 248A includes a plurality of blood vessel bifurcations, and a 3D model from probe data is suitable for the registration.

Referring to FIG. 4C, at process 450, the processor may provide instructions to the operator to move the instrument 230 toward the estimated probe areas 246 and 248 shown in image data, such that the probe device 220 scans the estimated probe areas 246 and 248 in the image data 300. The estimated probe areas 246 and 248 correspond to the target probe areas 246 and 246 of the anatomic model 245 respectively, and may be generated based on a registration (e.g., a less accurate registration without using any probe data) between the anatomic model 245 and the image data 300. In some embodiments, the instructions may indicate whether the probe data is collected for a 2D model or a 3D model. In the example of a 2D model (e.g., for estimated probe area 246B), the instruction may include a probe device direction/orientation aligned with the 2D cross-section direction which is aligned with the probe device direction/orientation. In the example of a 3D model (e.g., for estimated probe area 248B), the instruction may include a plurality of probe device direction/orientations such that the collected probe data is sufficient for 3D reconstruction of the probe area.

At process 460, the probe data is registered to the image data to generate a first registration. Various image registration algorithms may be used, including for example, intensity-based registration, feature-based registration, registration with linear transformation models, registration with non-rigid transformation models, etc. Process 460 may generate a first registration (e.g., a first transformation model) between the probe device space and the imaging device space. An example registration process of process 460 is described in detail below with reference to FIGS. 6A and 6B. In some embodiments, after the registration process of registering the probe data to the image data is completed, a computer-aided design (CAD) model of the probe device 220 may be superimposed on the image data in one or more displays of medical system 10, such as one or more displays of console 16 based on the first registration. For example, the location of the CAD model of the probe device 220 on the image data may be determined based on the first registration. In some embodiments, the probe data (e.g., an ultrasound image/video) may be superimposed (with or without the CAD model of the probe device 220) on the image data in the display based on the first registration.

At process 470, the anatomic model is registered to the probe data to generate a second registration. Various image registration algorithms may be used, including for example, intensity-based registration, feature-based registration, registration with linear transformation models, registration with non-rigid transformation models, etc. Process 460 may generate a second registration (e.g., a second transformation model) between the probe device space and the imaging device space. In some embodiments, a full scan of the anatomic feature 240 by the probe device is performed. In such embodiments, reconstruction (2D or 3D) of the entire anatomic feature is performed based on the full scan. For example, 3D reconstruction may be performed using both the probe data and the depth map from the image data 300. Such a full scan may be time-consuming and computationally expensive.

Alternatively, as described in detail below with reference to FIG. 7, in some embodiments, only partial scanning of the anatomic feature 240 by the probe device 220 (e.g., probe areas 246, 248) is needed for the registration. Probe data from each of the probe areas may be used for either 2D or 3D registration. In an example, a 2D image from probe data of probe area 246 may be used to register probe data with the 3D anatomic model (e.g., using cross sections of the 3D anatomic model). In another example, a 3D model from probe data of probe area 248 may be used to register probe data with the 3D anatomic model.

In various embodiments, various types of anatomic feature information may be determined using the probe data from the probe device 220, which may be used to improve the second registration. In some examples, those types of information from the probe data may not be available from the image data from the imaging device 210. For example, the probe device 220 provides ultrasound images of the anatomic feature 240 with color doppler, which may provide blood flow information of the vessels of the anatomic feature 240 (e.g., by superimposing colors on the image to indicate speed and direction of blood flow in the vessel). In some embodiments, the anatomic model (e.g., a 3D model including blood flow information of the vessels) may be registered to the probe data by matching those types of information (e.g., blood flow information of the vessels) in in the anatomic model and the probe data. In some embodiments, the registration is performed by registering a 3D anatomic model with a 2D image (e.g., a cross section including one or more vessels) of the probe data.

At process 480, the anatomic model is registered to the image data to generate a third registration. The third registration may be generated using the first registration and second registration. By incorporating the rich information provided by the probe device, accuracy of the third registration between the anatomic model and the image data is improved. In an example, at process 480, a third registration (e.g., a third transformation model) between the model space associated with the anatomic model and the imaging device space associated with the image data is determined by combining the first registration (e.g., the first transformation model) and the second registration (e.g., the second transformation model). In an example, the anatomic model is registered to the image data by transforming the anatomic model using the second registration. That transformed anatomic model in the probe device space is then registered to the image data by transforming the transformed anatomic model in the probe device space to the imaging device space using the first registration.

At process 490, the registered anatomic model using the third registration is displayed with the image data on one or more displays of medical system 10, such as one or more displays of console 16. Referring to the example of FIG. 4D, an anatomic model 245 is superimposed on the image data 300 in a display based on the third registration between the model space and the imaging device space. In some embodiments, one or more procedures (e.g., surgical, diagnostic, therapeutic, or biopsy procedure(s)) are performed (e.g., by an operator using a medical instruction) on the anatomic feature based on the third registration (e.g., based on the registered anatomic model).

FIG. 5 is a simplified diagram of a method 500 for automatically detecting activation of a probe device according to some embodiments. According to some embodiments consistent with FIG. 4A, method 500 may generally correspond to process 420 of method 400.

At process 510, one or more probe activity signals associated with activities of the probe device are received. In some embodiments, the probe activity signals may include a variety of signals that are correlated with activity or inactivity of the probe device. For example, the probe activity signals may include one or more of the following: the pose of the medical instrument; the grasping position of the end effector of the medical instrument (e.g., certain poses and grasping positions may be correlated with the operator gripping the probe device with the medical instrument); the probe data (e.g., the presence or absence of reflections in ultrasound probe data may be used to distinguish whether the probe device is interacting with air, tissue, or another material); instrument kinematics; the orientation of the probe device relative to standard or valid orientations of the probe device when being gripped by the medical instrument; or the like.

At process 520, activation status of the probe device is determined automatically based on the probe activity signals. Various activation status determination algorithms may be used to determine the activation status of the probe device. In an example, at process 530, the activation status is determined by comparing the probe activity signals to predetermined activation thresholds. In that example, a processor may determine that the probe device is in an activated status if the probe activity signals exceed the predetermined thresholds, and determine that the probe device is in an inactivated status if the probe activity signals do not exceed the predetermined thresholds. In another example, at process 540, trained decision trees are used to determine the activation status of the probe device. In yet another example, at process 550, a neural network model (e.g., a machine learning model) may be used to determine the activation status of the probe device. In some embodiments, a processor may further determine that the probe device is in an activated status after determining that the probe device (e.g., an ultrasound probe) touches the target anatomic feature.

At process 560, the automatically determined activation status of the probe device is provided by the processor (e.g., the processors of control system 20). In some embodiments, detection of an activation status (e.g., when switching between an activated status and an inactivated status) may cause a probe device activation status message to be displayed to the operator through a display system. In some embodiments, if it is determined that the probe device 220 has an activated state, the method 400 may proceed to processes 430 through 490 for receiving probe data from the probe device 220 and performing a registration from an anatomy model to imaging data based on the probe data. In some embodiments, if it is determined that the probe device 220 has an inactivated state, the method 400 may wait until it is detected that the probe device 220 is in an activated state.

Referring to the example of FIG. 6, illustrated is a simplified diagram of a method 600 for registering probe data to image data according to some embodiments. According to some embodiments consistent with FIG. 4A, method 600 may generally correspond to process 440 of method 400. As described in detail below, an initial registration between the probe device space and the imaging device space may be determined based on the kinematics of the imaging device and medical instrument controlling the probe device, and the initial registration may be fine-tuned based on the probe device information in the image data.

At process 610, an initial registration from the probe device space to the imaging device space is estimated based on kinematics of the imaging device and/or the medical instrument, and a projection of a probe device relative to the image data is predicted based on the initial registration. In some embodiments, the initial registration includes an initial transformation with one or more initial transformation parameters (e.g., translative parameters, scale parameters, etc.). The initial registration, including its registration parameters, may be determined based on the kinematics of the imaging device (e.g., the endoscope), the kinematics of the medical instrument, and the position and orientation of the probe device relative to the medical instrument (e.g., determined based on a pose of the end effector of the medical instrument gripping the probe device).

Referring to FIG. 6B, a predicted projection 650 of the probe device based on the initial registration from the probe device space to the imaging device space is illustrated. In an example, the predicted projection 650 of the probe device corresponds to an expected outline that the probe device is expected to occupy in the image data (e.g., endoscope image) based on the initial registration.

At process 620, the predicted projection 650 of the probe device is compared to an actual projection of the probe device in the image data. An image alignment algorithm (e.g., 2D or 3D image alignment algorithms) may be used to align the predicted projection 650 with the actual projection of the probe device 220 (e.g., an actual outline of the probe device) in the image data.

At process 630, the initial registration (including its registration parameters) is updated based on the comparison of the predicted projection of the probe device to match the actual projection of the probe device. In an example, a registration update algorithm iteratively updates the one or more registration parameters such that the predicted projection of the probe device based on the updated registration match the actual projection of the probe device. In an example, an optimizer may be used to generate a registration that minimizes a similarity metric (e.g., providing a scalar value that describes the similarity) between the predicted projection 650 and the actual projection of the probe device 220.

At process 640, the probe data is registered to the image data based on the updated registration (including its updated registration parameters).

FIG. 7 is a simplified diagram of a method 700 for registering the anatomic model to the probe data according to some embodiments. According to some embodiments consistent with FIG. 4A, method 700 may generally correspond to process 460 of method 400. As discussed in detail below, in method 700, a partial scan, instead of a full scan, of the entire anatomic feature may be performed to register the anatomic model to the probe data, which reduces computational time, provides a quicker feedback to an operator, and saves computational power.

At process 710, one or more target attributes (e.g., probe areas 246 and/or 248) of the anatomic feature is identified based on the anatomic model. In an example, a target attribute may include one or more segmented features, also referred to as anatomic feature elements (e.g., a vasculature of the kidney, particular blood vessel bifurcation(s) in the vasculature, etc.), of the anatomic feature based on the anatomic model.

At process 720, probe data of the particular portions (e.g., probe areas 246 and/or 248) of the anatomic feature are obtained (e.g., by instructing an operator to scan the probe areas) using the probe device. 2D or 3D image of the probe areas from probe data are used to identify corresponding target attributes in the probe data and the anatomic model. Various image processing algorithms may be used to map the features in the probe data and the anatomic model.

At process 730, the anatomic model is registered to the probe data based on the target attribute(s) as identified in the probe data and the corresponding target attribute in the anatomic model.

Some examples of processors may include non-transient, tangible, machine readable media that include executable code that when run by one or more processors may cause the one or more processors to perform the processes of methods 400-700. Some common forms of machine readable media that may include the processes of methods 400-700 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A medical system, comprising:
   one or more processors configured to perform operations comprising:
   receiving image data associated with an anatomic feature of a patient from a first imaging device, the image data associated with a first imaging device space;
   obtaining probe data associated with the anatomic feature from a probe device, the probe data associated with a probe device space;
   registering the probe data to the image data to generate a first registration between the probe device space and the first imaging device space;
   registering an anatomic model associated with the anatomic feature to the probe data to generate a second registration between a model space of the anatomic model and the probe device space;
   transforming, based on the second registration, the anatomic model to the probe device space to generate a first transformed anatomic model;
   transforming, based on the first registration, the first transformed anatomic model to the first imaging device space to generate a second transformed anatomic model; and
   superimposing and displaying a visual representation of the second transformed anatomic model over the image data.

2. The medical system of claim 1, wherein the probe device is an accessory device lacking independent movement capabilities.

3. The medical system of claim 1, further comprising:
   a manipulator configured to control the probe device by controlling an end effector to grip the probe device.

4. The medical system of claim 3, wherein the obtaining the probe data associated with the anatomic feature from the probe device includes:
   controlling the probe device, by the manipulator, to scan at least a portion of the anatomic feature.

5. The medical system of claim 3, wherein the operations include:
   determining that the probe device is in an activated state; and
   in response to the determination that the probe device is in the activated state, registering the probe data to the image data to generate the first registration.

6. The medical system of claim 5, wherein the determining that the probe device is in the activated state includes automatically determining that the probe device is in the activated state based on one or more of:
   probe device activity signals associated with the probe device;
   trained decision trees associated with activation states of the probe device; or
   a neural network model associated with activation states of the probe device.

7. The medical system of claim 1, wherein the registering the probe data to the image data includes:
   determining an initial registration between the probe device space and the first imaging device space to generate a predicted projection of the probe device relative to the image data; and
   generating the first registration based on updating the initial registration by comparing the predicted projection to an actual projection of the probe device in the image data.

8. A method, comprising:
   receiving image data associated with an anatomic feature of a patient from a first imaging device, the image data associated with a first imaging device space;
   obtaining probe data associated with the anatomic feature from a probe device, the probe data associated with a probe device space;
   registering the probe data to the image data to generate a first registration between the probe device space and the first imaging device space;
   registering an anatomic model associated with the anatomic feature to the probe data to generate a second registration between a model space of the anatomic model and the probe device space;
   transforming, based on the second registration, the anatomic model to the probe device space to generate a first transformed anatomic model;
   transforming, based on the first registration, the first transformed anatomic model to the first imaging device space to generate a second transformed anatomic model; and
   superimposing and displaying a visual representation of the second transformed anatomic model over the image data.

9. The method of claim 8, wherein the probe device is an accessory device lacking independent movement capabilities.

10. The method of claim 8, further comprising:
    controlling, by a manipulator, the probe device by controlling an end effector to grip the probe device.

11. The method of claim 10, wherein the obtaining the probe data associated with the anatomic feature from the probe device includes:
    controlling the probe device, by the manipulator, to scan at least a portion of the anatomic feature.

12. The method of claim 8, wherein the registering the probe data to the image data includes:
    determining an initial registration between the probe device space and the first imaging device space to generate a predicted projection of the probe device relative to the image data; and
    generating the first registration based on updating the initial registration by comparing the predicted projection to an actual projection of the probe device in the image data.

13. A non-transitory machine-readable medium comprising a plurality of machine-readable instructions which when executed by one or more processors associated with a medical device are adapted to cause the one or more processors to perform a method comprising:

receiving image data associated with an anatomic feature of a patient from a first imaging device, the image data associated with a first imaging device space;

obtaining probe data associated with the anatomic feature from a probe device, the probe data associated with a probe device space;

registering the probe data to the image data to generate a first registration between the probe device space and the first imaging device space;

registering an anatomic model associated with the anatomic feature to the probe data to generate a second registration between a model space of the anatomic model and the probe device space;

transforming, based on the second registration, the anatomic model to the probe device space to generate a first transformed anatomic model;

transforming, based on the first registration, the first transformed anatomic model to the first imaging device space to generate a second transformed anatomic model; and superimposing and displaying a visual representation of the second transformed anatomic model over the image data.

14. The non-transitory machine-readable medium of claim 13, wherein the method further comprises:

controlling, by a manipulator, the probe device by controlling an end effector to grip the probe device.

15. The non-transitory machine-readable medium of claim 14, wherein obtaining the probe data associated with the anatomic feature from the probe device includes:

controlling the probe device, by the manipulator, to scan at least a portion of the anatomic feature.

\* \* \* \* \*